United States Patent
Perassinoto et al.

(10) Patent No.: US 10,123,541 B2
(45) Date of Patent: Nov. 13, 2018

(54) BIOCIDAL MIXTURE, USE OF BIOCIDAL MIXTURE AND COMPOSITIONS COMPRISING A BIOCIDAL MIXTURE

(71) Applicant: ISP Investments LLC, Wilmington, DE (US)

(72) Inventors: Nelson Luís Perassinoto, São Paulo (BR); Maria Regina Bartuccio Raponi, São Paulo (BR); Tatiana Miyashiro Kumayama, América (BR); Juliana Luri Yoshida Shitara, São Paulo (BR); Juliana Garcia Da Silva, São Paulo (BR)

(73) Assignee: ISP INVESTMENTS LLC, Wilmington, DE (US)

( * ) Notice: Subject to any disclaimer, the term of this patent is extended or adjusted under 35 U.S.C. 154(b) by 0 days.

(21) Appl. No.: 15/122,314

(22) PCT Filed: Feb. 27, 2015

(86) PCT No.: PCT/US2015/017933
§ 371 (c)(1),
(2) Date: Aug. 29, 2016

(87) PCT Pub. No.: WO2015/131018
PCT Pub. Date: Sep. 3, 2015

(65) Prior Publication Data
US 2016/0366893 A1 Dec. 22, 2016

(30) Foreign Application Priority Data
Feb. 27, 2014 (BR) ........................ 10 2014 0048499

(51) Int. Cl.
*A01N 65/08* (2009.01)
*A01N 33/08* (2006.01)
*A61K 8/41* (2006.01)
*A61K 8/97* (2017.01)
*A61Q 17/00* (2006.01)
*A61Q 17/04* (2006.01)
*A61Q 19/00* (2006.01)
*A61Q 19/10* (2006.01)

(52) U.S. Cl.
CPC ............. *A01N 65/08* (2013.01); *A01N 33/08* (2013.01); *A61K 8/41* (2013.01); *A61K 8/97* (2013.01); *A61Q 17/005* (2013.01); *A61Q 17/04* (2013.01); *A61Q 19/00* (2013.01); *A61Q 19/10* (2013.01); *A61K 2800/592* (2013.01); *A61K 2800/77* (2013.01)

(58) Field of Classification Search
None
See application file for complete search history.

(56) References Cited

U.S. PATENT DOCUMENTS

| 6,379,720 B1 * | 4/2002 | Cooper ................. A01N 65/08 424/405 |
| 2004/0175480 A1 | 9/2004 | Seman et al. |
| 2011/0244030 A1 * | 10/2011 | Lebel ...................... A61K 9/12 424/450 |
| 2013/0005807 A1 * | 1/2013 | Ishida ..................... A61K 8/34 514/546 |

FOREIGN PATENT DOCUMENTS

| WO | WO2007071089 A1 | 6/2007 |
| WO | WO2007117433 A2 | 10/2007 |

OTHER PUBLICATIONS

Richards et al., Journal of Pharmaceutical Sciences, 62: 2035-2037 (1973).*
Kelly et al., Infectious Diseases Society of America, Poster Abstract (Abstract) (2011).*
Hopsteiner, "Beta Bio 45%" accessed at http://www.hopsteinercom/wp-content/uploads/2016/02/SS_Beta_Bio_45.pdf on Jun. 8, 2017.*
Hopsteiner Products Antibacterial, Website archived Apr. 8, 2013, accessed at https://web.archive.org/web/20130408052039/http://hopsteiner.com:80/products/antibacterial.php, Jan. 12, 2018. (Year: 2013).*
Rhodia Inc. Hops, as hops beta acids. Dec. 19, 2000.
International Search Report of PCT Publication No. WO 2015/131018 A1.

* cited by examiner

*Primary Examiner* — Alton N Pryor
(74) *Attorney, Agent, or Firm* — Thompson Hine LLP; William J. Davis

(57) ABSTRACT

The present invention generally relates to a synergistic mixture of biocidal effect comprising phenylpropanol and hop extract. Particularly, the mixture of the invention can be used in the fields of cosmetics, medicines and food.

7 Claims, No Drawings

BIOCIDAL MIXTURE, USE OF BIOCIDAL MIXTURE AND COMPOSITIONS COMPRISING A BIOCIDAL MIXTURE

CROSS-REFERENCE TO RELATED APPLICATIONS

This application is a national phase of PCT Application Number PCT/US2015/017933 filed Feb. 27, 2015 which claims priority from Brazilian Application Number BR 10 2014 004849 9 filed on Feb. 27, 2014 to which applicants claim the benefits of priority under 35 USC § 119(e) and 365, and which both applications are fully incorporated herein by reference.

The present invention generally relates to a biocidal mixture of synergistic effect comprising phenylpropanol and hop extract. Particularly, the mixture of the invention is used in the fields of cosmetics, medicines and food.

BACKGROUND OF THE INVENTION

Antibacterial properties of hop (*Humulus lupulus*) are known, particularly of strobile (female flowers) extract, used mainly as beer additive, which has flavoring and stabilizing effects, responsible for its bitter spicy taste. It is also known that the presence of beta-acids in strobile extracts provide antimicrobial properties, especially against Gram-positive bacteria and certain algae.

Phenylpropanol is known as a solvent for fragrances and odor masking agents.

Until now, no combinations with biocidal effect are known comprising both hop extract and phenylpropanol. The closest detected prior art was the international patent application WO2012175626, which relates to the treatment or prevention of scars, claiming an onion extract and liposomes further containing some optional ingredients, such as at least one preservative, such as phenylpropanol, among others, and/or at least one more active principle, such as hop extract, among many others. This document, which has an object completely different from the instant invention, neither mentions nor suggests the concomitant presence of hop extract and phenylpropanol, and also does not mention or suggest some effect issued from this combination.

It has been found, in accordance with the present invention, that non disclosed state of the art combinations of hop extract with phenylpropanol surprisingly present an important synergistic biocidal effect, which is as effective as of the one provided by known biocides.

According to the meaning used herein, the use of hop extract also includes the use of beta-acids per se, even if not contained in hop extract.

DESCRIPTION OF THE INVENTION

The present invention generally refers to a biocidal mixture characterized by comprising hop extract and phenylpropanol.

In a particular embodiment of the invention, not excluding any other, hop extract is rich in beta-acids, such as lupulone, colupulone and adlupulone either as free base or as metal salts, such as potassium salt. Advantageously, hop extract contains about 45±1.5% w/w of beta-acids.

In a particular embodiment of the invention, not excluding any other, the ratio between hop extract containing about 45% of beta-acids and phenylpropanol is comprised between 1:30 and 1:50. This particular range is equivalent to an approximate ratio of 1:66 to 1:112 between the contents of beta-acids and phenylpropanol.

It is important to point out the effects that the increase in hop extract content in relation to phenylpropanol content provide to the invention mix: a darker brown color and a spicy flavor develop, as well as the mixture cost increases. In view of such aspects, a person skilled in the art knows to set a more adequate ratio to specific needs or possibilities.

In a particular embodiment, the synergistic biocidal mixture of the invention contains, additionally to the hop extract and phenylpropanol components, one or more active principles and one or more non-active ingredients, such as vehicle or diluent.

Another aspect of the invention is the use of the synergistic biocidal mixture, in the preparation of cosmetic, pharmaceutical or food compositions.

Another aspect of the invention are compositions, particularly useful in cosmetic, pharmaceutical or food fields, comprising the biocidal mixture of the invention in amounts between 0.05 and 5% w/w, more particularly between 0.1 and 1% w/w.

The use of the mixture of invention in such compositions can be in different ways:
- the two components, hop extract (or beta-acids) and phenylpropanol, are premixed;
- the two isolated components, are concurrently or consecutively added during the preparation of said composition;
- two independent formulations, each comprising one of the components of the mixture are concomitantly or consecutively added during the preparation of said composition.

Without excluding other alternatives, shampoos, conditioners, liquid soaps, lotions and sunscreens, among others, are examples of compositions of the invention in the cosmetic field.

EXAMPLES

The following examples are merely illustrative of the invention, which is not limited to the same. Moreover, such examples do not impose limitations to the invention beyond those contained in the attached claims.

Example 1

Minimum Inhibitory Concentration ("MIC")

This example intends to analyze the microbial activity of the mixture of invention compared to the individual activity of the mixture components using the methodology that determines the minimal concentration of the substance or mixture that inhibits microorganism growth.

The tested micro-organisms were:

*Staphylococcus aureus*, ATCC 6538

*Escherichia coli*, ATCC 8739

*Pseudomonas aeruginosa*, ATCC 9027

*Burkholderia cepacia*, ATCC 25416

*Candida albicans*, ATCC 10231

*Aspergillus brasiliensis*, ATCC 16404

The tested samples were:

| SAMPLE | DESCRIPTION |
|---|---|
| 1 | Phenylpropanol |
| 2 | Hop extract with 45% beta-acids |
| 3 | mixture 1 + 2 (97.5% phenylpropanol and 2.5% hop extract) |
| 4 | Control: "Liquid Germall Plus" (*) |

(*) 39.60% diazolidinyl urea, 0.40% iodopropynyl butylcarbamate and 60% propylene glycol, provided by Ashland Inc.

The methodology employed was as follows:

The samples of the table above were initially prepared with an initial concentration of 3% based on their solubility in water, and then diluted to achieve the following concentrations: 1.5%; 0.75%; 0.375%; 0.1875%; 0.09375%.

The dilutions were obtained as follows: (a) to a first test tube containing 5 mL of tripticase soy broth (TSB), 5 mL of 3% concentration solution were added and the mixture was vortexed. 5 mL of the contents of this tube were removed and added to a second tube containing 5 mL of TSB and the mixture was vortexed. This procedure was repeated until obtaining the various concentrations.

The tested organisms were prepared as typical organism inoculants, under the form of a saline suspension. The concentration of bacterial inoculants was approximately $1 \times 10^6$ cfu/mL ("colony-forming unit per milliliter"). The concentration of fungal inoculants was approximately $1 \times 10^5$ spores/mL. In the sequence, each sample solution was inoculated with 0.1 mL of organism inoculum and vortexed. The tubes containing bacteria were incubated for 24 hours at 35° C. and the tubes containing fungi were incubated for 48 hours at 25° C.

An aliquot of 0.1 mL from these tubes was transferred to a tube having 9 mL of Letheen broth containing neutralizing agents. These Letheen tubes were again incubated for 48 hours with Letheen under incubation temperature for bacteria or fungi. Then, a swab previously wet with TSB was put in contact with sample solutions with concentrations 1.5%; 0.75%; 0.375%; 0.1875% and 0.09375%, and then they were swiped over the surface of culture plates (for bacteria: Letheen agar, AOAC—Association of Official Analytical Chemists; for fungi: Mycophil® agar of low pH with Tween® 20 polysorbate surfactant).

The table below shows the results obtained concerning the growth of organisms:

| Sample/Tubes Letheen | S. aureus | E. coli | P. aeruginosa | B. cepacia | C. albicans | A. brasiliensis |
|---|---|---|---|---|---|---|
| 1-1.5% | + | + | − | + | − | − |
| 1-0.75% | + | + | + | + | − | − |
| 1-0.375% | + | + | + | + | + | + |
| 1-0.1875% | + | + | + | + | + | + |
| 1-0.09375% | + | + | + | + | + | + |
| 2-1.5% | − | − | − | − | + | + |
| 2-0.75% | + | + | + | + | + | + |
| 2-0.375% | + | + | + | + | + | + |
| 2-0.1875% | + | + | + | + | + | + |
| 2-0.09375% | + | + | + | + | + | + |
| 3-1.5% | − | − | − | − | − | − |
| 3-0.75% | − | − | − | − | − | − |
| 3-0.375% | − | + | − | − | + | + |
| 3-0.1875% | + | + | + | + | + | + |
| 3-0.09375% | + | + | + | + | + | + |
| 4-1.5% | − | + | − | − | − | − |
| 4-0.75% | + | + | + | − | − | − |
| 4-0.375% | + | + | + | − | + | + |
| 4-0.1875% | + | + | + | + | + | + |
| 4-0.09375% | + | + | + | + | + | + |

Caption
− = no growth
+ = low growth
++ = moderate growth
+++ = high growth

The table above shows that component 1, even at a concentration of 1.5%, was not able to inhibit the growth of certain microorganisms (S. aureus, E. coli, B. cepacia); component 2, also at a concentration of 1.5%, did not inhibit the growth of other microorganisms (C. albicans and A. brasilliensis). Surprisingly, according to the invention, the combination of the two components (at a rate of 2.5% of hop extract and 97.5% of phenylpropanol) at 0.75% was effective in inhibiting all microorganisms evaluated. This clearly denotes a synergistic effect between the two components that is not attained if used separately.

Pursuant to the understanding herein adopted, the definition of synergy, in the galenic formulations field, is: in a controlled mixture, the indicative of synergistic effect is when the combined effect of 2 or more ingredients in a given concentration is greater than the sum of the individual contribution of each ingredient.

Example 2—SPF 30 Sunscreen Lotion

A sunscreen lotion was prepared with a sun protection factor (SPF) of 30 with 0.5% of the mixture of the invention, to test its antibacterial efficacy.

Table 1 below provides information on the ingredients.

TABLE I list of ingredients and sunscreen lotion phases, SPF 30

| INGREDIENTS | % w/w |
|---|---|
| PHASE A | |
| water | Qsp to 100 |
| Di-sodium EDTA | 0.05 |
| Glycerin | 1.50 |
| Triethanolamine | 0.04 |
| acrylic acid/vinylpyrrolidone copolymer with low crosslink density (1) | 0.40 |
| PHASE B | |
| Butyl methoxydibenzoylmethane (2) | 3.50 |
| Ethylhexyl salicylate (3) | 3.00 |
| Octocrylene (ester formed by condensing diphenyl cyanoacrylate with 2-ethylhexanol) (4) | 7.00 |
| Glyceryl stearate and laureth-23 (5) | 1.50 |
| Tridecyl neopentanoate (6) | 3.00 |
| Vinylpyrrolidone/eicosene copolymer (7) | 2.00 |
| Titanium dioxide/phenethyl benzoate/isocetyl stearate and stearoyl (8) | 5.00 |
| Bis-ethylhexyloxyphenol methoxyphenyl triazine (9) | 3.30 |
| Homosalate (3.3.5-trimethylcyclohexyl 2-hydroxybenzoate) | 9.50 |
| PHASE C | |
| Potassium Cetyl phosphate | 1.50 |
| PHASE D | |
| Triethanolamine | 0.25 |
| PHASE E | |
| Cyclopentasiloxane (10) | 0.50 |
| PHASE F | |
| Disodium lauriminodipropionate tocopheryl phosphates (11) | 0.50 |
| 96% denaturated alcohol | 1.50 |
| Biocidal mixture of the invention (item 3 of example 1) | 0.50 |

(1) UltraThix ™ P100, marketed by Ashland, a U.S. Company
(2) Escalol ™ 517, marketed by Ashland, a U.S. Company
(3) Escalol ™ 587, marketed by Ashland, a U.S. Company.
(4) Escalol ™ 597, marketed by Ashland, a U.S. Company.
(5) Cerasynt ™ 945, marketed by Ashland, a U.S. Company.
(6) Ceraphyl ™ 55, marketed by Ashland, a U.S. Company.
(7) Antaron ™ V-220, marketed by Ashland, a U.S. Company.
(8) Escalol ™ Block, marketed by Ashland, a U.S. Company.
(9) Escalol ™ S, marketed by Ashland, a U.S. Company.
(10) Si-Tec ™ CM 040, marketed by Ashland, a U.S. Company.
(11) Vital ET ™ Product, marketed by Ashland, a U.S. Company.

Preparation Procedure
1—The phase A components were combined, homogenized until dispersion and heated up to 83-88° C.
2—The phase B components were combined under mixing and heated up to 83-88° C. Phase B was added to phase A.
3—At 83-88° C., phase C was added to phase AB, under stirring for 10 minutes. The mixture was further stirred using a turrax mixer for 5 minutes.
4—Phase D was added. It was homogenized for 5 minutes.
5—At 40° C., phase E was added and homogenized for 5 minutes.
6—Then, the mixture was cooled to 30-35° C. and the ingredients of phase F were added separately, homogenizing after every addition.
7—pH was adjusted to 6-7.2, as needed.

Example 3—Liquid Soap

A liquid soap formulation was prepared from table II below, with 0.2% of the mixture of the invention, to test its antibacterial efficacy.

| INGREDIENTS | % w/w |
|---|---|
| PHASE A | |
| water | Qsp To 100 |
| Di-sodium EDTA | 0.10 |
| Citric acid (20% solution) | 0.10 |
| Polyquaternium 28 (1) | 0.50 |
| Sodium laureth sulfate (27%) | 30.00 |
| PHASE B | |
| Cocamidopropyl betaine (30%) | 10.00 |
| Castoryl Maleate (2) | 0.50 |
| Polysorbate 20 | 1.00 |
| PHASE C | |
| Cocamide diethylamine (90%) | 3.50 |
| PHASE D | |
| Biocidal mixture of the invention (item 3 of example 1) | 0.20 |

(1) Gafquat ™ HS100, marketed by Ashland, a U.S. Company.
(2) Ceraphyl ™ RMT, marketed by Ashland, a U.S. Company.

Preparation Procedure:
1. The components of Phase A were added in the order indicated above, under stirring, until complete solubilization of the components.
2. In a second vessel, the components of Phase B were mixed under stirring. This phase B was added to phase A.
3. The component of Phase C was added to the previous mixed phases under stirring.
4. The component of Phase D was added to the previous mixed phases under stirring.

Example 4—Simulation of Effectiveness of Shelf Life for the Formulations of Examples 2 and 3

The microorganisms mentioned in example 1 were prepared from pure cultures and individually inoculated.

In each of 6 test vials, 30 g of the product sample from example 2 (and example 3) were added and 0.3 mL of solution containing inoculum of a different organism was added to each of these vials to reach $10^6$ cfu/g of product. Efficient stirring was needed to disperse the inoculum.

After inoculation, consecutive dilutions of the samples were made using neutralizing solution (Letheen broth) in the first dilution, and transferring the solution the Petri dishes, to which TSA culture medium (tripticase soy agar) was added for bacteria and SDA (Sabouraud and dextrose agar) culture medium was added for fungi. Incubation of plates containing TSA was at 35° C. for 48 hours, and of plates containing SDA, it was performed at 28° C. for 5 days.

This procedure was repeated after 48 hours, 7, 14, 21 and 28 days after the first inoculation, for counting microorganisms. A re-inoculation was made on the $21^{th}$ day of the test.

The following tables show the results of the challenge test:

Challenge test results for the formulation of example 2 (I=inoculation and R=re-inoculation):

| SAMPLES WITH INOCULUM | DAYS | | | | | |
|---|---|---|---|---|---|---|
| | $1^{st}$ day | $3^{rd}$ day | $7^{th}$ day | $14^{th}$ day | $21^{st}$ day | $28^{th}$ day |
| S. aureus | <10 | <10 | <10 | <10 | <10 | <10 |
| E. coli | <10 | $1.80 \times 10^4$ | <10 | <10 | <10 | <10 |
| P. aeruginosa | <10 | <10 | <10 | <10 | <10 | <10 |
| B. cepacea | <10 | <10 | <10 | <10 | <10 | <10 |
| C. albicans | <10 | $3.50 \times 10^2$ | <10 | <10 | <10 | <10 |
| A. brasiliensis | <10 | <10 | $7.00 \times 10^2$ | $1.10 \times 10^2$ | $4.10 \times 10^2$ | <10 |

Challenge test results for the formulation of example 3 (I=inoculation and R=re-inoculation):

| SAMPLES WITH INOCULUM | DAYS | | | | | |
|---|---|---|---|---|---|---|
| | 1° dia 1 | 3° dia 48 h | 7° dia | 14° dia | 21° dia R | 28° dia |
| S. aureus | <10 | <10 | <10 | <10 | <10 | <10 |
| E. coli | <10 | <10 | <10 | <10 | <10 | <10 |
| P. aeruginosa | <10 | <10 | <10 | <10 | <10 | <10 |
| C. albicans | <10 | <10 | <10 | <10 | <10 | <10 |
| A. brasiliensis | <10 | <10 | <10 | <10 | <10 | <10 |

The challenge test is typically performed by the manufacturers of cosmetic products to demonstrate that their products will not be subject to decomposition, instability and/or degradation by microbiological contamination within their period of validity. When a certain percentage of the mixture object of this invention is used in cosmetic products, which were of 0.2% and 0.5% in the examples presented herein, results of the challenge test where these products were inoculated with standardized microorganisms showed that, after 28 days, there were no microbes due to the action of the mixture of the instant invention.

Example 5—Synergistic Effect of the Biocidal Blend

The microorganisms mentioned in example 1 were prepared from pure cultures and individually inoculated and a body lotion formulation was challenged with these microorganisms as described in example 4.

After inoculation, consecutive dilutions of the samples were made using neutralizing solution (Letheen broth) in the first dilution, and transferring the solution the Petri dishes, to which TSA culture medium (tripticase soy agar) was added for bacteria and SDA (Sabouraud and dextrose agar) culture medium was added for fungi. Incubation of plates containing TSA was at 35° C. for 48 hours, and of plates containing SDA, it was performed at 28° C. for 5 days.

This procedure was repeated after 48 hours, 7, 14, 21 and 28 days after the first inoculation, for counting microorganisms. A re-inoculation was made on the $21^{th}$ day of the test.

The following tables show the results of the challenge test:

Challenge test results for the formulation containing no preservatives (control sample) (I=inoculation and R=re-inoculation):

| Samples with Inoculum | Challenge Test - "In-can" Days of analysis | | | | | |
|---|---|---|---|---|---|---|
| Without preservative | 1° day 1 | 3° day 48 h | 7° day | 14° day | 21° day R | 28° day |
| Body Lotion # 12018-1C S. aureus | <10 | $2.30 \times 10^3$ | <10 | <10 | <10 | $1.66 \times 10^8$ |
| Body Lotion # 12018-1C E. coli | <10 | $1.15 \times 10^3$ | $7.00 \times 10^2$ | <10 | <10 | $1.28 \times 10^6$ |
| Body Lotion # 12018-1C P. aeruginosa | <10 | $1.02 \times 10^4$ | $9.50 \times 10^3$ | $3.10 \times 10^2$ | $1.20 \times 10^5$ | $1.59 \times 10^6$ |
| Body Lotion # 12018-1C B. cepacea | <10 | $2.56 \times 10^4$ | $8.20 \times 10^3$ | $5.80 \times 10^2$ | $3.90 \times 10^5$ | $7.90 \times 10^8$ |
| Body Lotion # 12018-1C C. albicans | <10 | $1.30 \times 10^7$ | $1.10 \times 10^7$ | $2.70 \times 10^4$ | $1.12 \times 10^3$ | $8.70 \times 10^5$ |
| Body Lotion # 12018-1C A. brasiliensis | <10 | $1.30 \times 10^5$ | $8.00 \times 10^4$ | $9.00 \times 10^4$ | $8.00 \times 10^4$ | $1.60 \times 10^5$ |

Challenge test results for the formulation containing biocide blend at 0.5% (I=inoculation and R=re-inoculation):

| Samples with Inoculum | Challenge Test - "In-can" Days of analysis | | | | | |
|---|---|---|---|---|---|---|
| | 1° day 1 | 3° day 48 h | 7° day | 14° day | 21° day R | 28° day |
| Body Lotion # 12018-1E S. aureus | <10 | <10 | <10 | <10 | <10 | <10 |
| Body Lotion # 12018-1E E. coli | <10 | <10 | <10 | <10 | <10 | <10 |
| Body Lotion # 12018-1E P. aeruginosa | <10 | <10 | <10 | <10 | <10 | <10 |
| Body Lotion # 12018-1E B. cepacea | <10 | <10 | <10 | <10 | <10 | <10 |
| Body Lotion # 12018-1E C. albicans | <10 | <10 | <10 | <10 | <10 | <10 |
| Body Lotion # 12018-1E A. brasiliensis | <10 | $9.00 \times 10^2$ | $1.40 \times 10^2$ | $2.40 \times 10^2$ | <10 | <10 |

Challenge test results for the formulation containing phenylpropanol 0.5% (I=inoculation and R=re-inoculation):

| Samples with Inoculum | Challenge Test - "In-can" Days of analysis | | | | | |
|---|---|---|---|---|---|---|
| 0.5% Phenylpropanol | 1° day 1 | 3° day 48 h | 7° day | 14° day | 21° day R | 28° day |
| Body Lotion # 12018-33A S. aureus | <10 | <10 | <10 | <10 | <10 | <10 |
| Body Lotion # 12018-33A E. coli | <10 | <10 | <10 | <10 | <10 | <10 |
| Body Lotion # 12018-33A P. aeruginosa | <10 | <10 | <10 | <10 | <10 | <10 |
| Body Lotion # 12018-33A B. cepacea | <10 | <10 | <10 | <10 | <10 | <10 |
| Body Lotion # 12018-33A C. albicans | <10 | <10 | <10 | <10 | <10 | <10 |
| Body Lotion # 12018-33A A. brasiliensis | <10 | $1.20 \times 10^3$ | $1.90 \times 10^3$ | $1.00 \times 10^3$ | <10 | $8.00 \times 10^3$ |

Challenge test results for the formulation containing Hop Extract with 45% beta-acids 0.5% (I=inoculation and R=re-inoculation):

| Samples with Inoculum | Challenge Test - "In-can" Days of analysis | | | | | |
|---|---|---|---|---|---|---|
| | 1° day 1 | 3° day 48 h | 7° day | 14° day | 21° day R | 28° day |
| Body Lotion # 12018-33B S. aureus | <10 | <10 | <10 | <10 | <10 | <10 |
| Body Lotion # 12018-33B E. coli | <10 | <10 | <10 | <10 | <10 | <10 |

-continued

| Samples with Inoculum | 1° day 1 | 3° day 48 h | 7° day | 14° day | 21° day R | 28° day |
|---|---|---|---|---|---|---|
| Body Lotion # 12018-33B *P. aeruginosa* | <10 | <10 | <10 | <10 | <10 | <10 |
| Body Lotion # 12018-33B *B. cepacea* | <10 | <10 | <10 | <10 | <10 | $2.70 \times 10^2$ |
| Body Lotion # 12018-33B *C. albicans* | <10 | $1.27 \times 10^6$ | $1.10 \times 10^6$ | $2.80 \times 10^2$ | $1.77 \times 10^4$ | $1.60 \times 10^6$ |
| Body Lotion # 12018-33B *A. brasiliensis* | <10 | $7.00 \times 10^4$ | $1.30 \times 10^5$ | $6.00 \times 10^5$ | <10 | $1.40 \times 10^8$ |

Challenge Test - "In-can" Days of analysis

The results of these challenge tests show the better performance of the biocidal blend when compared to the individual component at same use levels.

Based on the information and examples presented herein, a person skilled in the art can carry out the invention by equivalent forms, i.e., even if not expressly described, in a functional manner, and attain results of the same nature as the described invention, therefore within the scope of appended claims.

The invention claimed is:

1. A biocidal mixture comprising hop extract and phenylpropanol, wherein the hop extract comprises beta-acids either as free bases or as metal salts and wherein the weight ratio of beta-acids to phenylpropanol provides synergistic activity.

2. The biocidal mixture according to claim 1, wherein the hop extract comprises 45% w/w of beta-acids selected from lupulone, colupulone, adlupulone, and combination thereof.

3. The biocidal mixture according to claim 1, further comprising one or more active principles and one or more vehicles or diluents.

4. A composition comprising a biocidal mixture of claim 1.

5. The composition according to claim 4, wherein the composition is a cosmetic composition, a pharmaceutical composition, or a food composition.

6. The composition according to claim 4, wherein the composition comprises between 0.05% and 5% w/w of the biocidal mixture.

7. The composition according to claim 4, wherein the composition comprises between 0.1% and 1% w/w of the biocidal mixture.

* * * * *